(12) United States Patent
Hwang

(10) Patent No.: US 10,363,433 B2
(45) Date of Patent: Jul. 30, 2019

(54) DRUSEN TREATMENT METHOD AND METHOD FOR CONTROLLING DRUSEN TREATMENT DEVICE

(71) Applicant: Lutronic Vision Inc, Burlington, MA (US)

(72) Inventor: Hae Lyung Hwang, Seoul (KR)

(73) Assignee: LUTRONIC VISION INC, Burlington, MA (US)

( * ) Notice: Subject to any disclaimer, the term of this patent is extended or adjusted under 35 U.S.C. 154(b) by 47 days.

(21) Appl. No.: 14/763,087

(22) PCT Filed: Jan. 23, 2014

(86) PCT No.: PCT/KR2014/000684
§ 371 (c)(1),
(2) Date: Jul. 23, 2015

(87) PCT Pub. No.: WO2014/116045
PCT Pub. Date: Jul. 31, 2014

(65) Prior Publication Data
US 2015/0343236 A1    Dec. 3, 2015

Related U.S. Application Data

(60) Provisional application No. 61/755,954, filed on Jan. 23, 2013.

(51) Int. Cl.
*A61B 3/12* (2006.01)
*A61B 5/01* (2006.01)
(Continued)

(52) U.S. Cl.
CPC ............. *A61N 5/0625* (2013.01); *A61B 3/12* (2013.01); *A61F 9/008* (2013.01); *A61B 5/01* (2013.01);
(Continued)

(58) Field of Classification Search
CPC .......... A61N 5/0625; A61N 2005/0627; A61N 2005/0662; A61N 2005/067;
(Continued)

(56) References Cited

U.S. PATENT DOCUMENTS

2004/0039378 A1* 2/2004 Lin ..................... A61B 18/20
606/6
2004/0176752 A1  9/2004 Alfano et al.
(Continued)

FOREIGN PATENT DOCUMENTS

WO    WO 2011/050056 A2    4/2011

OTHER PUBLICATIONS

Johann Roider et al., "Variability of RPE reaction in two cases after selective RPE laser effects in prophylactic treatment of drusen", Graefe's Archive for Clinical and Experimental Ophthalmolgoy, 1999, pp. 45-50, vol. 237, No. 1, Springer-Verlag.
(Continued)

*Primary Examiner* — Lynsey C Eiseman
*Assistant Examiner* — Jessandra F Hough

(57) ABSTRACT

A drusen treatment method includes confirming a location of drusen in a fundus of a patient; determining a treatment area by including a location on which the drusen exists; and removing the drusen by transferring energy to the treatment area.

19 Claims, 9 Drawing Sheets

(51) Int. Cl.
*A61N 5/06* (2006.01)
*A61F 9/008* (2006.01)
*A61N 5/067* (2006.01)

(52) U.S. Cl.
CPC .............. *A61F 2009/00844* (2013.01); *A61F 2009/00863* (2013.01); *A61N 2005/067* (2013.01); *A61N 2005/0627* (2013.01); *A61N 2005/0662* (2013.01)

(58) Field of Classification Search
CPC .... A61N 2008/0627; A61B 3/12; A61B 5/01; A61F 9/008; A61F 2009/00844; A61F 2008/00863; A61F 2009/00863
See application file for complete search history.

(56) References Cited

U.S. PATENT DOCUMENTS

2007/0213693 A1* 9/2007 Plunkett ................ A61F 9/008
606/6
2010/0049180 A1* 2/2010 Wells .................... A61N 5/0616
606/12
2014/0243805 A1* 8/2014 Dick .................... A61F 9/00823
606/11
2016/0174830 A1* 6/2016 Rubin .................... A61B 3/102
351/206

OTHER PUBLICATIONS

C Framme et al., "Autofluorescence imaging after selective RPE laser treatment in macular diseases and clinical outcome: a pilot study", British journal of ophthalmology, 2002, pp. 1099-1105, vol. 86, No. 10.

International search report for PCT/KR2014/000684 filed on Jan. 23, 2014.

* cited by examiner

DRUSEN TREATMENT METHOD AND METHOD FOR CONTROLLING DRUSEN TREATMENT DEVICE

BACKGROUND OF THE INVENTION

Field of the Invention

The present invention relates to a drusen treatment method and a method for controlling a drusen treatment device, and more specifically, to a drusen treatment method and a method for controlling a drusen treatment device that remove drusen by transferring energy to an area with drusen accumulations.

Related Art

A retina is a sensitive neural layer that is positioned on the fundus area of an eyeball to sense light. The macula is present at the center of the retina and neural cells called photoreceptors are collected at the macula. The photoreceptors are structured to emit light when illuminated and the macula with dense photoreceptors plays a critical role to view objects and maintain the central view.

FIG. 1 is a cross-sectional view schematically illustrating the cross-sectional structure of a fundus. As shown in FIG. 1, a photoreceptor P including a plurality of cell layers is provided on the fundus area. At a lower side of the photoreceptor P are positioned the retinal pigmented epithelium cell (RPE cell) R and the Bruch's membrane B, and at a lower side of the Bruch's membrane is positioned the choroid C where a blood vessel passes. The choroid C supplies oxygen and nutrients to the inside of the retina through the Bruch's membrane B, and the RPE cell R supports the photoreceptor P while delivering the oxygen and nutrients supplied through the Bruch's membrane B to the photoreceptor P.

As aging proceeds, wastes created in the retina are primarily accumulated in a space between the RPE cell R and the Bruch's membrane B or inside the Bruch's membrane B. The wastes are called drusen D. As drusen D are accumulated between the RPE cell R and the Bruch's membrane B, the RPE cell layer is separated from the Bruch's membrane B, thus causing dry age related macular degeneration. Further, as drusen D are accumulated, an inflammation occurs, secreting vascular endothelial growth factor (VEGF). This prompts the growth of new blood vessels. The new blood vessels grow into the retina, penetrating the weakened Bruch's membrane B, and thus, serious wet age related macular degeneration may develop. In a worse case, the vision may be lost.

A widely used treatment method for such retina-related disease is antiangiogenic therapy to prevent the formation of new blood vessels. This method is to inject an anti-VEFG to suppress the abnormally growing VEGF, thereby stopping the vessel formation process. However, such treatment merely suppresses the growth of additional vessels and fails to completely respond to the same because drusen are still present between the RPE cell and the Bruch's membrane. Accordingly, continuous treatment should be followed to prevent the formation of more vessels.

SUMMARY OF THE INVENTION

The present invention addresses the above issues and aims to provide a treatment method for fully removing the drusen left between the RPE cell and the Bruch's membrane.

To achieve the above objects, according to the present invention, there is provided a drusen treatment method comprising identifying a position of drusen located in a patient's fundus, determining a treatment area including the position where the drusen are located, and transferring energy to the treatment area to remove the drusen.

Here, the energy transferred to the treatment area may improve functions by which fundus tissues in the treatment area discharge the drusen to a choroid. Specifically, the energy transferred to the treatment area may improve a function by which a retinal pigment epithelium (RPE) cell adjacent to the drusen discharges a waste between the RPE cell and a Bruch's membrane to an outside of the Bruch's membrane.

Here, transferring the energy to the treatment area is configured to transfer the energy to an RPE cell adjacent to the drusen. Transferring the energy to the treatment area is configured to transfer the energy by radiating light to the treatment area. Here, the amount of the radiated light absorbed by the choroid in the treatment area may be smaller than the amount of the radiated light absorbed by the RPE cell and larger than the amount of the radiated light absorbed by the photoreceptor. Specifically, the radiated light may have a wavelength of 510 nm to 590 nm.

The radiated light may selectively increase a temperature of the RPE cell in the treatment area. In particular, a width at which a temperature of the choroid in the treatment area is increased by the radiated may be smaller than a width at which the temperature of the RPE cell is increased and may be larger than a width at which the photoreceptor is increased. Specifically, the radiated light may be pulse-type laser, and the laser may have a pulse width of 5 microseconds or less.

Here, the step of transferring the energy to the treatment area may do thermal damage to the RPE cell in such a level as to induce regeneration of the RPE cell. The step of transferring the energy to the treatment area may be to terminate the energy transfer based on a signal generated from the treatment area.

The step of determining the treatment area may be to set a boundary of the treatment area to an outside of a boundary where the drusen are located to be formed to be larger than the area where the drusen are located. Specifically, the step of determining the treatment area may be to determine to include the RPE cell located two to fifteen cells away from the boundary of the area where the drusen are located.

On the other hand, the objects of the present invention may also be achieved by a method for controlling a drusen treatment device comprising determining a treatment area based on a position of drusen present in a fundus, transferring energy to the treatment area, and terminating the energy transfer based on a signal sensed in the treatment area.

According to the present invention, in addition to restricting the lesion from further getting worse, drusen, the cause of the lesion, may be removed to enable complete treatment and restoration of the lesion.

Further, the treatment method goes on in a non-invasive way using light, thus minimizing the patient's pain or resistance to the treatment.

DESCRIPTION OF EXEMPLARY EMBODIMENTS

Figure 1:
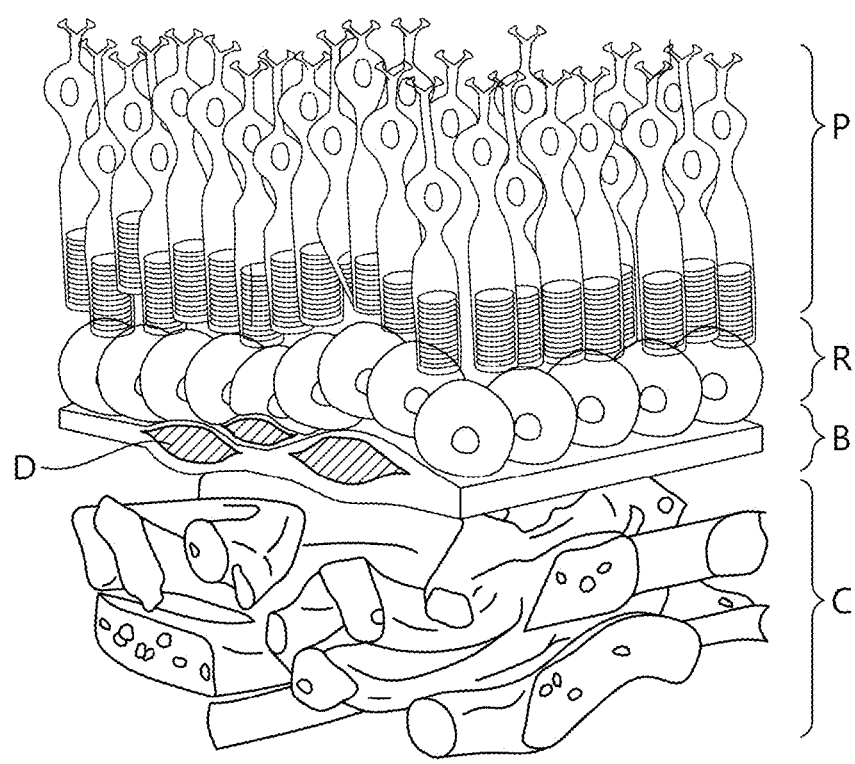
FIG. 1 is a cross-sectional view schematically illustrating a cross-sectional structure of a fundus.

Hereinafter, a drusen treatment method and method for controlling a drusen treatment device according to an embodiment of the present invention are described with reference to the drawings. In the following description, the locational relationship between the elements is shown primarily with respect to the drawings. The views in the drawings may be exaggerated as necessary or to simplify the structure of the present invention for ease of description. Accordingly, the present invention is not limited thereto, and other various devices may be added or changes or omissions may be made to the present invention.

As described above, a fundus tissue includes a photoreceptor P including a multi-layered structure of optic nerves, an RPE cell layer R, and a Bruch's membrane B forming a boundary with the choroid C. The RPE cell layer R supplies oxygen and nutrients from the vessel of the choroid C to the photoreceptor P through the Bruch's membrane B and discharges wastes created from the photoreceptor P through the Bruch's membrane B to the vessel of the choroid C. Separation is rendered to arise between the RPE cell layer R and the Bruch's membrane B by the drusen that are accumulated between the RPE cell layer R and the Bruch's membrane B or in the inside of the Bruch's membrane B as the fundus tissue is aged. Accordingly, an insufficient amount of nutrients and oxygen is supplied to the RPE cell layer R and the photoreceptor P positioned with the drusen D accumulations, deteriorating various functions (a main cause of dry age related macular degeneration). Further, the deficiency of oxygen arising due to the drusen may induce the formation of new blood cells which then penetrate into the RPE cell layer and the Bruch's membrane, causing a high chance of the occurrence of wet age related macular degeneration.

Accordingly, according to the present invention, there is provided a drusen treatment method for removing the drusen by applying energy to the area where the drusen are accumulated. Here, the energy provided to the area with the drusen D accumulations may be light energy. Various types of light may come in use. According to the instant embodiment, a laser beam with good wavelength selectivity is put to use. However, other various light sources, such as a laser, a laser diode, an LED, and a lamp, may be used.

Figure 2:
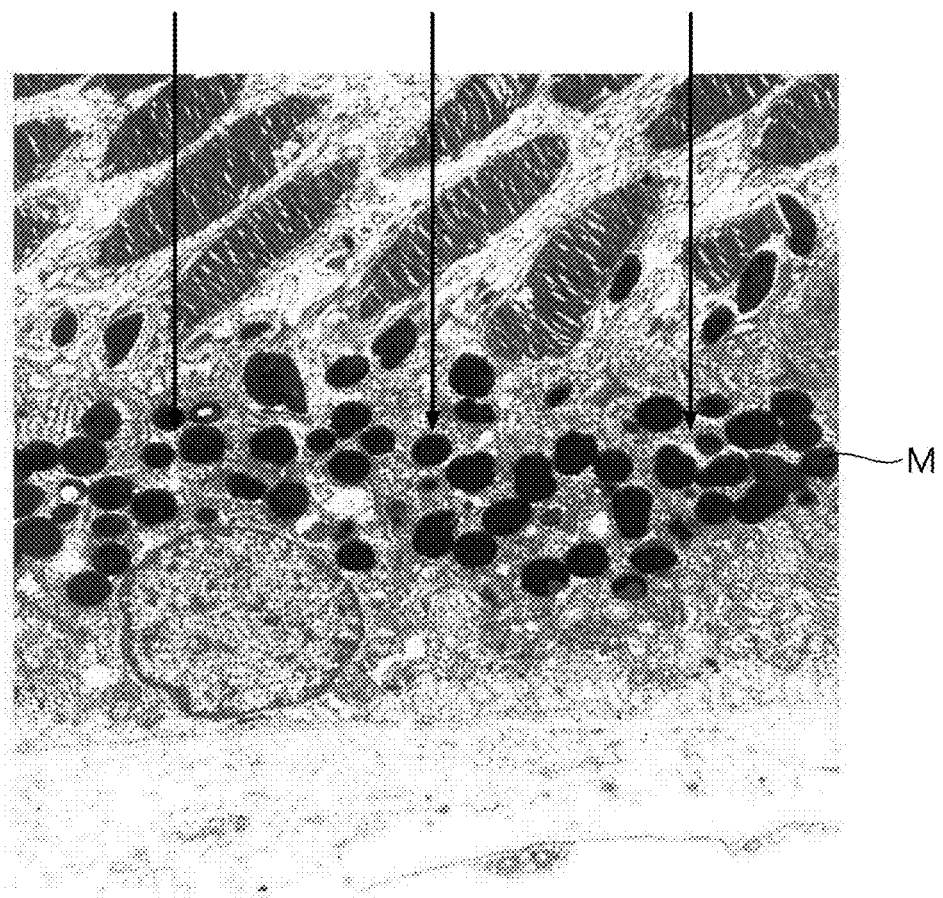
FIG. 2 is a view schematically illustrating the characteristics of light radiated to an RPE layer in a retina.

As shown in FIG. 2, light of a wavelength with good absorption characteristics may be applied to the RPE cell layer containing pigment such as a melanosome M, and light with poor absorption may be applied to the photoreceptor. In such case, damage to the photoreceptor may be minimized.

A test result shows that light with a wavelength of 510 nm to 590 nm is nearly not absorbed by the photoreceptor P and is rather substantially transmitted. The light of the wavelength is absorbed by the RPE cell layer R by 50% or more, and part of the light passing through the RPE cell layer R is absorbed by the choroid C. Such nature is shown more noticeable for light with a wavelength of 520 nm to 540 nm.

As such, as the area with the drusen D accumulations is energized, the fundus tissues adjacent to the drusen are rendered to present improved characteristics in a predetermined time, discharging the drusen present between the RPE cell layer and the Bruch's membrane or inside the Bruch's membrane towards the choroid. This is considered to come from an improvement in the pumping characteristics, i.e., transportation, of the RPE cell layer.

Figure 3:
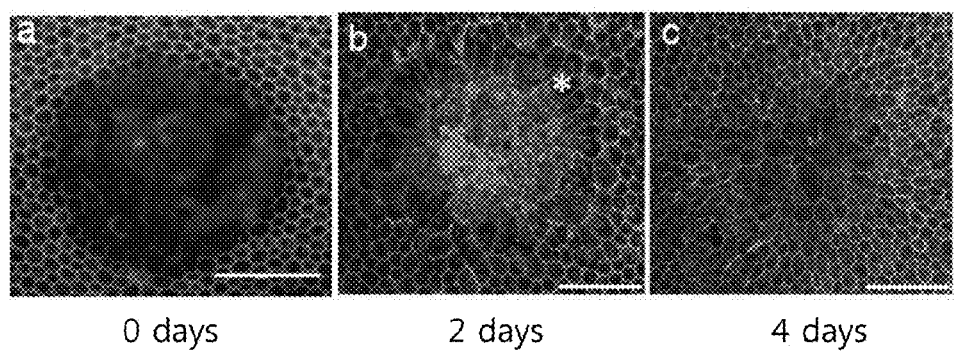
FIG. 3 is a picture illustrating an example in which an RPE cell layer and the choroid are thermally damaged and then cultured.

The RPE cell is an excellent self-regeneratable tissue. This may also be verified from the result obtained by culturing the RPE cell layer and choroid thermally damaged by selective light radiation, as shown in FIG. 3. Accordingly, as the RPE cell layer is damaged by radiating a wavelength of light with good tissue selectivity, the RPE cell layer actively proceeds with the self-regeneration process, restoring the various functions deteriorated due to aging. By such regeneration process, the RPE cell layer R has an improved pumping characteristic, thus making better the characteristic that the drusen D is discharged to the outside of the Bruch's membrane B.

Figure 4:
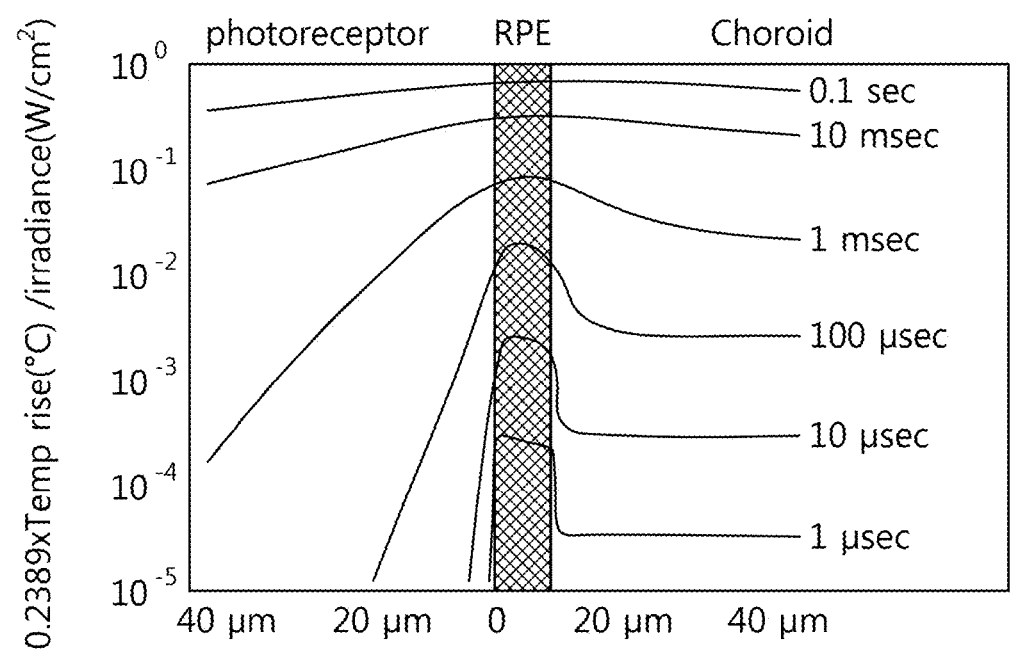
FIG. 4 is a graph illustrating a temperature distribution of a fundus tissue according to light pulse widths.

Here, as shown in FIG. 4, the fundus tissue may experience different temperature rise characteristics depending on pulse widths of light radiation as shown in FIG. 4. Although the photoreceptor P absorbs little light, a photoreceptor P adjacent to the RPE cell layer R with good light absorption characteristic may go through a temperature rise due to the heat transferred from the RPE cell layer. Thus, what may be used is light having a pulse width that may minimize damage to the photoreceptor P while selectively raising the temperature of the RPE cell layer to cause thermal damage thereto, and the pulse width of the light (the pulse width is the duration when one pulse of pulse-type light is radiated) may be not more than 5 us. Such characteristics may be more noticeable when the pulse width is not more than 2 us, and the light with a wavelength of 520 nm to 540 nm, when it has a pulse width of substantially 1.7 us, has been observed to present such characteristics better. In this case, the RPE cell layer R experiences a largest temperature rise, and the temperature of the choroid C is subjected to a steady rise. However, the photoreceptor P, even though positioned adjacent to the RPE cell layer R, experiences little rise in temperature.

Figure 5:
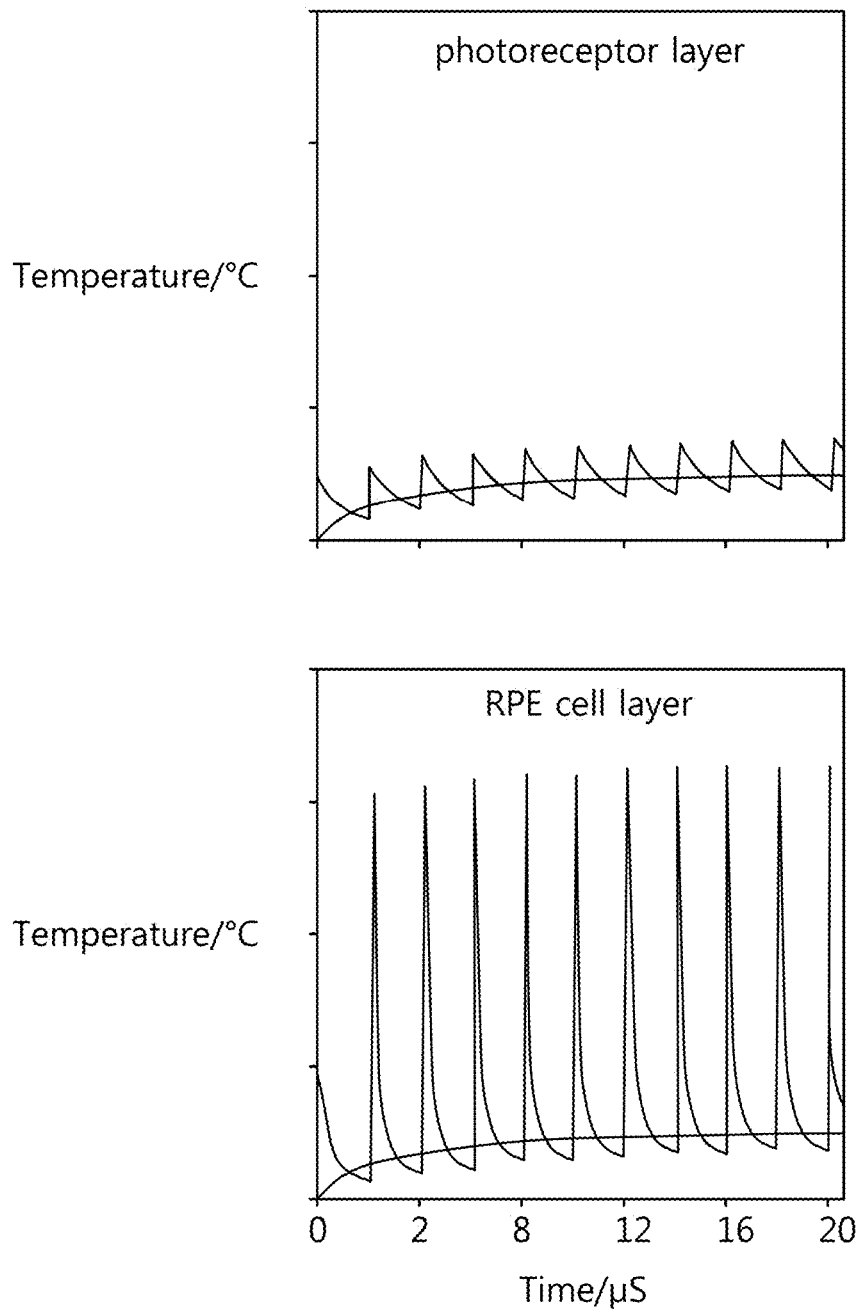
FIG. 5 is a graph illustrating a temperature variation of a fundus tissue upon radiation of pulse-type light.

FIG. 5 is a graph illustrating a temperature variation of the RPE cell layer and the photoreceptor when illuminated with pulse laser. As shown in FIG. 5, the RPE cell layer R, when radiated with light, presents a temperature rise high enough to cause thermal damage thereto for each pulse. By contrast, the photoreceptor P, although showing a tiny temperature variation for each pulse, fails to reach a level at which damage occurs. As such, the present invention may induce the regeneration of the RPE cell without damaging the photoreceptor through selective retina treatment.

As set forth above, energy provided may be of level at which the adjacent photoreceptor P is prevented from damage and the incurred thermal damage is done so that the RPE cell R may go on with self-regeneration. Thus, the supply of energy to the spot where the drusen D are accumulated may be terminated based on a predetermined signal generated from the tissue.

Figure 6:
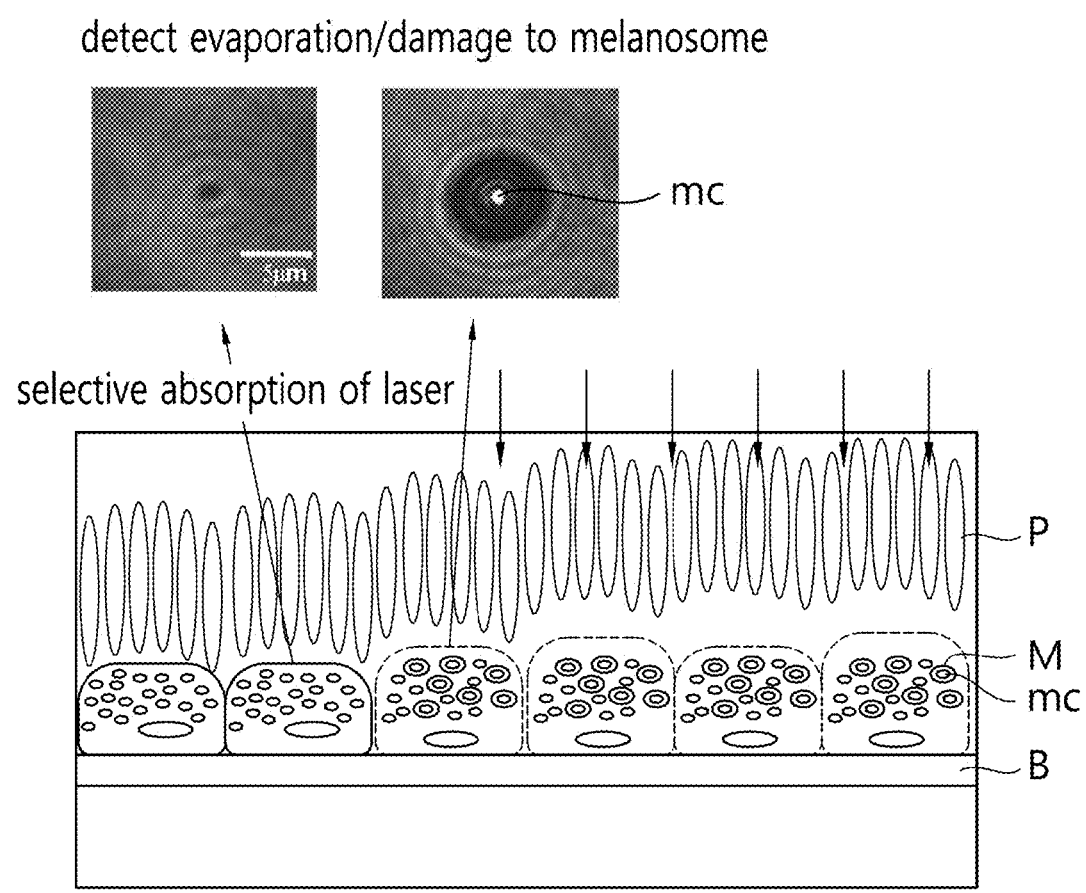
FIG. 6 is a cross-sectional view illustrating an example in which a fundus tissue absorbs laser to create a variation.

Here, the signal generated from the tissue may mean various signals. The signal may be a signal created by the thermal damage by the energy provided, and such signal may be in various forms such as an optical signal, a sound wave-wise signal, or an electrical signal. What may be used among them may be a signal generated by a micro cavitation (mc) created as the melanosome M of the RPE cell R, upon light radiation, absorbs the energy and thus the temperature rises. As shown in FIG. 6, the RPE cell radiated with light is expanded due to the creation of the micro cavitation as the temperature rises. Whether the micro cavitation occurs may be sensed by analysis of light reflected, and use of the same enables the sensing of whether the RPE cell R is thermally damaged and then the control as to whether to provide energy.

By the above-described method, when energy is applied to the area where the drusen D are created, adjacent tissues, such as the RPE cell layer R or the Bruch's membrane B, present improved discharge characteristics, thus enabling the elimination of the drusen D towards the choroid. In such case, the energy may be selectively provided to the RPE cell layer at the corresponding position, so that the pumping capability of the RPE cell layer may be improved by the vigorous self-regeneration capability of the RPE cell while preventing damage to the adjacent photoreceptor.

Figure 7:
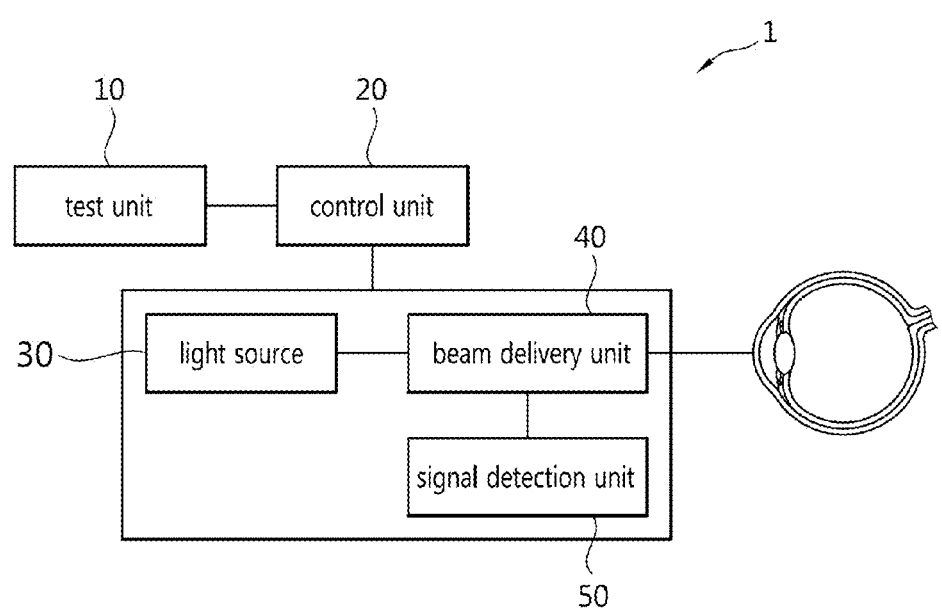
FIG. 7 is a block diagram schematically illustrating a drusen treatment device according to an embodiment of the present invention.
Figure 8:
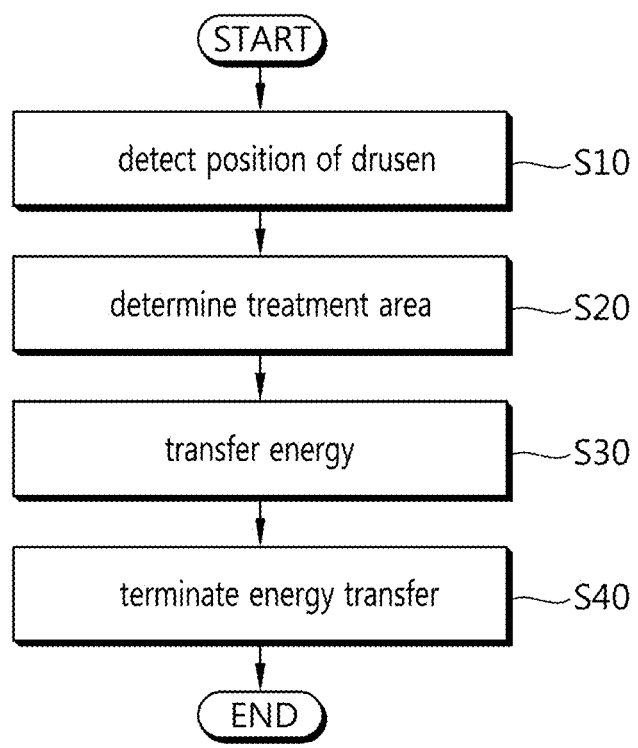
FIG. 8 is a flowchart illustrating a drusen treatment method according to an embodiment of the present invention.

Now described in further detail are a drusen treatment method and drusen treatment device for implementing the same, using the above description with reference to FIGS. 7 and 8.

FIG. 7 is a block diagram schematically illustrating a drusen treatment device according to an embodiment of the present invention. FIG. 8 is a flowchart illustrating a drusen treatment method according to an embodiment of the present invention.

As shown in FIG. 7, the drusen treatment device may include a test unit 10, a control unit 20, a light source 30, a beam delivery unit 40, and a signal detection unit 50.

The test unit 10 may be a device for identifying the position of drusen D. Various fundus picturing devices that may detect the position of drusen may be used as the test unit 10. The test unit 10 may be provided integrally with the drusen treatment device or separately from the drusen treatment device.

The control unit 20 may set a treatment area based on the information on the position of drusen identified by the test unit 10. The control unit 20 may be configured to control the content of driving the light source 30 and the beam delivery unit 40 and may adjust the output and radiation pattern of light radiated to the treatment area.

The light source 30 generate light energy to be transferred to the treatment area. In this case, the light source 30 radiates a wavelength of light that has a high absorption characteristic to the RPE cell layer R to induce thermal damage to the RPE cell layer R and that has a pulse width at which the photoreceptor P may be prevented from damage, thereby enabling SRT treatment. As an example, in the present embodiment, the light generated may have a wavelength of 510 nm to 590 nm, more specifically, 527 nm, and a pulse width of 5 us or less, more specifically, 1.7 us.

The beam delivery unit 40 is a component that transfers light generated from the light source 30 to the treatment area. The beam delivery unit 40 may include a plurality of scanners constituted of reflecting mirrors and various optic components. The beam delivery unit 40 is controlled by the control unit 20 and enables light to be radiated to a preset position of the treatment area according to a preset pattern.

Meanwhile, the signal detection unit 50 may detect a signal transferred from the treatment area. When the light is radiated to the treatment area by the beam delivery unit 40, the tissue of the treatment area is varied by the transferred energy, and accordingly, various forms of signals may be presented. The signal detection unit 50 may identify whether the treatment area experiences a tissue variation by detecting the signals. In the instant embodiment, it may be configured so that the occurrence of micro cavitation in the RPE cell R may be detected through sound wave information reflected or phase information on the reflected light when light is radiated.

Although the drusen treatment device 1 according to the present invention has been schematically described, this is merely an exemplary configuration for describing the present invention, and various changes may be made thereto.

In connection with FIG. 8, a drusen treatment method and method for controlling the treatment device using the drusen treatment device 1 of FIG. 7 are described. First, the step of detecting the position of drusen to treat the drusen D is performed (S10). This step is performed by the test unit 10, such as the above-described fundus picturing device or fundus tomography device, and an image captured by the test unit 10 may be analyzed to detect the position L1 of the drusen distributed in the fundus.

Figure 9:
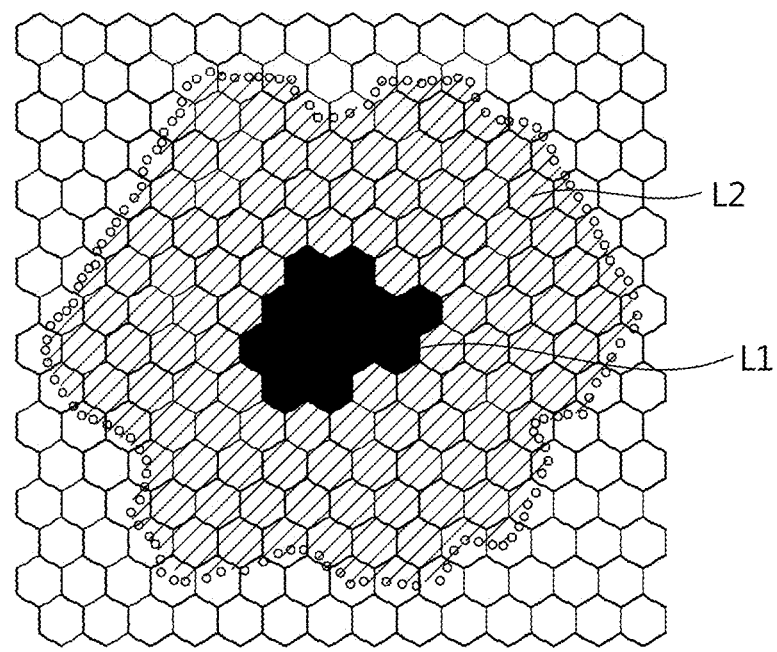
FIG. 9 is a view schematically illustrating the step of determining a treatment area in FIG. 8.

When the position L1 of the drusen is detected, the step of determining a treatment area L2 may be conducted (S20). The treatment area L2 may be determined to include the position L1 of the drusen. The tissues involving the discharge of the drusen D are involved in tissues at exactly the same position as the drusen as well as tissues positioned adjacent thereto. Accordingly, the step of determining the treatment area, as shown in FIG. 9, may be set to be larger than the area where the drusen are positioned by setting a boundary of the treatment area L2 to be outside the boundary of the area where the drusen is located.

The boundary of the treatment area L2 may be set to be 10 um to 200 um or more away from the boundary of the area where the drusen is positioned. As another example, the boundary of the treatment area may be set to include the position where two through up to 15 RPE cells are positioned apart from the boundary of the area where the drusen are positioned.

Meanwhile, when the treatment area is determined, the step of transferring energy to the treatment area is performed (S30). In the step of transferring energy to the treatment area, the wavelength, pulse width, and radiation pattern of light may be determined by the control of the control unit 20, and the light source 30 and the beam delivery unit 40 may be driven corresponding to the same, thereby transferring energy. Here, as described above, light that has a wavelength of 510 nm to 590 nm, specifically, 527 nm, and a pulse width of 5 microseconds or less, specifically, 1.7 microseconds, may be radiated.

As such, when the energy is transferred to the treatment area, the energy, by its wavelength nature, is absorbed primarily by the RPE cell layer R, so that the RPE cell layer R goes through a temperature rise and resultantly thermal damage. In this step, the light is partially absorbed by the choroid C as well as by the RPE cell layer that may then thus experience a temperature rise. However, the light may substantially pass through the photoreceptor P rather than being absorbed.

While the instant step goes on, the signal detection unit 50 may be configured to measure and detect a signal generated from the fundus by the continuous energy transfer. The signal here may be a signal generated by the thermal damage that is done to the fundus tissue by the transferred energy, specifically, a signal generated by a micro cavitation that may be created by the evaporation of the melanosome M inside the RPE cell layer R. In the energy transfer step, when radiating pulses of light to the same spot, the light output may be controlled to be increased for each pulse and be radiated in order to facilitate to reach the time of generation of the signal.

Upon sensing a signal originating from a tissue variation while energy is transferred to a particular spot of the treatment area, the control unit 20 may adjust the energy transferred to the treatment area based on the signal (S40). For example, when the micro cavitation is identified as occurring, control may be performed so that the RPE cell R at the position may be considered to have been thermally damaged sufficiently to perform a regeneration process, pausing the energy supply. Or, when the micro cavitation is identified as occurring, control may be conducted so that a predetermined radiation pattern of light is radiated from the time that the micro cavitation is identified and is then terminated.

It may be considered that the treatment is done at one spot through the above steps, and the radiation position may be changed to a next spot in the treatment area using the beam delivery unit, and the above-described treatment steps may then be repeatedly performed.

The above-described drusen treatment method may lead to improvements in functions of tissues adjacent to the position with the drusen accumulations, i.e., the RPE cell and Bruch's membrane, so that the drusen may be discharged to the choroid, thus enabling the removal of the drusen in the retina. Accordingly, fundamental treatment may be done for patients with dry age related macular degeneration while effectively cutting off the likelihood of developing to wet age related macular degeneration.

Although the present invention has been described in connection with embodiments thereof, the present invention is not limited thereto and various changes may be made thereto without departing from the scope of the present invention defined in the following claims.

What is claimed is:

1. A drusen treatment method, comprising:
   identifying a position of drusen located in a patient's fundus;
   determining a treatment area considering the position where the drusen are located; and
   decreasing the drusen by transferring energy to the treatment area,
   wherein determining the treatment area includes setting a boundary of the treatment area outside of an outer boundary of the drusen, a plurality of retinal pigment epithelium (RPE) cells being disposed between the outer boundary of the drusen and the boundary of the treatment area, a number of the plurality of RPE cells being in a range from two to fifteen, the outer boundary of the drusen and the boundary of the treatment area being on a surface that is perpendicular to a thickness of an RPE layer,
   wherein transferring energy to the treatment area includes sequentially radiating light on a plurality of spots located within the treatment area, and
   wherein transferring the energy to the treatment area includes transferring the energy to the entire treatment area that includes the plurality of RPE cells outside of the outer boundary of the drusen.

2. The drusen treatment method of claim 1, wherein the energy transferred to the treatment area improves functions by which fundus tissues in the treatment area discharge the drusen to a choroid.

3. The drusen treatment method of claim 1, wherein the energy transferred to the treatment area improves a function by which an RPE cell adjacent to the drusen discharges a waste between the RPE cell adjacent to the drusen and a Bruch's membrane to a space external to the Bruch's membrane.

4. The drusen treatment method of claim 1, wherein an amount of the radiated light absorbed by an RPE cell in the treatment area is larger than an amount of the radiated light absorbed by a photoreceptor in the treatment area.

5. The drusen treatment method of claim 4, wherein the amount of the radiated light absorbed by a choroid in the treatment area is smaller than the amount of the radiated light absorbed by the RPE cell in the treatment area, and larger than the amount of the radiated light absorbed by the photoreceptor.

6. The drusen treatment method of claim 4, wherein the radiated light has a wavelength of 510 nm to 590 nm.

7. The drusen treatment method of claim 1, wherein the radiated light selectively increases a temperature of an RPE cell in the treatment area.

8. The drusen treatment method of claim 7, wherein a temperature of the RPE cell in the treatment area is increased by light radiated to the treatment area, and a temperature of a photoreceptor in the treatment area is not substantially increased by the light radiated to the treatment area.

9. The drusen treatment method of claim 8, wherein a temperature rise of a choroid in the treatment area by the radiated light is smaller than a temperature rise of the RPE cell in the treatment area, and is larger than a temperature rise of a photoreceptor in the treatment area when the energy is transferred to the treatment area.

10. The drusen treatment method of claim 7, wherein the radiated light is pulse-type laser, and the laser has a pulse width of 5 microseconds or less.

11. The drusen treatment method of claim 1, wherein the plurality of RPE cells are a first plurality of RPE cells, and wherein transferring the energy to the treatment area causes thermal damage to a second plurality of RPE cells located in the treatment area, the thermal damage inducing regeneration of the second plurality of RPE cells in the treatment area.

12. The drusen treatment method of claim 11, further comprising:
   terminating the energy transfer based on a condition of the treatment area.

13. The drusen treatment method of claim 12, wherein the condition is a thermal variation in the second plurality of RPE cells.

14. A method for controlling a drusen treatment device, the method comprising:
   determining a treatment area based on a position of drusen present in a fundus;
   transferring energy to a first spot within the treatment area;
   terminating the energy transfer to the first spot based on a sensed condition of the treatment area; and
   transferring energy to a second spot within the treatment area,
   wherein determining the treatment area includes setting a boundary of the treatment area outside of an outer boundary of the drusen, a plurality of retinal pigment epithelium (RPE) cells being disposed between the outer boundary of the drusen and the boundary of the treatment area, a number of the plurality of RPE cells being in a range from two to fifteen, the outer boundary of the drusen and the boundary of the treatment area being on a surface that is perpendicular to a thickness of an RPE layer, and wherein energy is transferred to the entire treatment area that includes the plurality of RPE cells outside of the outer boundary of the drusen.

15. The method of claim 14, wherein the energy transferred to the treatment area improves a function by which an RPE cell adjacent to the drusen discharges a waste between the RPE cell adjacent to the drusen and a Bruch's membrane to a space external to the Bruch's membrane.

16. The method of claim 15, wherein the sensed condition of the treatment area is a thermal variation in the RPE cell adjacent to the drusen.

17. A method, comprising:

identifying, by a drusen treatment device, a position of drusen located in a fundus;

determining, by the drusen treatment device, a treatment area considering the position of the drusen, an outer boundary of the treatment area being defined outside of an outer boundary of the drusen, a plurality of retinal pigment epithelium (RPE) cells being disposed between the outer boundary of drusen and the boundary of the treatment area, a number of the plurality of RPE cells being in a range from two to fifteen, the outer boundary of the drusen and the boundary of the treatment area being on a surface that is perpendicular to a thickness of an RPE layer; and transferring, by the drusen treatment device, energy to the treatment area by sequentially radiating light on a plurality of spots within the treatment area, wherein transferring the energy to the treatment area includes transferring the energy to the entire treatment area that includes the plurality of RPE cells outside of the outer boundary of the drusen.

18. The drusen treatment method of claim 1, wherein decreasing the drusen by transferring energy to the treatment area includes decreasing the drusen by transferring energy to the treatment area without transferring energy outside of the treatment area.

19. The drusen treatment method of claim 1, wherein the treatment area includes a plurality of photoreceptors and a second plurality of RPE cells, and wherein sequentially radiating the light on the plurality of spots located within the treatment area includes causing thermal damage to the second plurality of RPE cells in the treatment area without causing thermal damage to the plurality of photoreceptors in the treatment area, the light having a wavelength of 510 nm to 590 nm.

* * * * *